(12) United States Patent
Schäfer et al.

(10) Patent No.: US 10,939,881 B2
(45) Date of Patent: Mar. 9, 2021

(54) GUIDANCE DEVICE FOR A TEE PROBE

(71) Applicant: KONINKLIJKE PHILIPS N.V., Eindhoven (NL)

(72) Inventors: Dirk Schäfer, Hamburg (DE); Eberhard Sebastian Hansis, Hamburg (DE); Niels Nijhof, Utrecht (NL); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 641 days.

(21) Appl. No.: 15/318,235

(22) PCT Filed: Jun. 10, 2015

(86) PCT No.: PCT/EP2015/062938
§ 371 (c)(1),
(2) Date: Dec. 12, 2016

(87) PCT Pub. No.: WO2015/193150
PCT Pub. Date: Dec. 23, 2015

(65) Prior Publication Data
US 2017/0105685 A1 Apr. 20, 2017

(30) Foreign Application Priority Data
Jun. 17, 2014 (EP) .................................... 14172641

(51) Int. Cl.
*A61B 6/12* (2006.01)
*A61B 8/08* (2006.01)
(Continued)

(52) U.S. Cl.
CPC ................ *A61B 6/12* (2013.01); *A61B 6/487* (2013.01); *A61B 8/0841* (2013.01);
(Continued)

(58) Field of Classification Search
CPC ......... A61B 6/12; A61B 8/463; A61B 8/5261; A61B 8/5223; A61B 6/487; A61B 8/4416;
(Continued)

(56) References Cited

U.S. PATENT DOCUMENTS 6,711,429 B1 * 3/2004 Gilboa ...................... A61B 5/06
600/407
6,996,430 B1 * 2/2006 Gilboa ...................... A61B 6/12
600/407
(Continued)

FOREIGN PATENT DOCUMENTS

DE 102007021061 A1 11/2008
JP 2012071178 A 4/2012
(Continued)

OTHER PUBLICATIONS

Haase, C. et al "Model based 3D CS-catheter tracking from 2D X-ray projections: Binary versus attenuation models", Computerized Medical Imaging and Graphics, 2013. Abstract Only.
(Continued)

*Primary Examiner* — Keith M Raymond
*Assistant Examiner* — Johnathan Maynard

(57) ABSTRACT

The present invention relates to a guidance device (10) for a TEE probe (20), a medical imaging system (1), a method for guiding a TEE probe (20), a computer program element for controlling such device and a computer readable medium having stored such computer program element. The guidance device (10) for a TEE probe (20) comprises an image data provision unit (11), and a processing unit (12). The image data provision unit (11) is configured to provide first image data showing an interventional device (40) and a TEE probe (20) in an initial position and orientation. The processing unit (12) is configured to determine a centerline of the interventional device (40) in the first image data. The
(Continued)

processing unit (12) is configured to determine a plane (41) orthogonal to a tangent of the centerline as viewing plane. The processing unit (12) is configured to calculate an imaging plane and an imaging orientation of the TEE probe (20) to lie approximately in the viewing plane. The processing unit (12) is configured to provide the calculated data as guidance data.

20 Claims, 3 Drawing Sheets

(51) Int. Cl.
*A61B 8/00* (2006.01)
*A61B 34/20* (2016.01)
*A61B 8/12* (2006.01)
*A61B 6/00* (2006.01)
*A61B 8/14* (2006.01)

(52) U.S. Cl.
CPC .............. *A61B 8/0883* (2013.01); *A61B 8/12* (2013.01); *A61B 8/4416* (2013.01); *A61B 8/463* (2013.01); *A61B 8/5223* (2013.01); *A61B 8/5261* (2013.01); *A61B 8/54* (2013.01); *A61B 8/14* (2013.01); *A61B 2034/2063* (2016.02); *A61B 2034/2065* (2016.02)

(58) Field of Classification Search
CPC ....... A61B 8/54; A61B 8/0883; A61B 8/0841; A61B 8/12; A61B 2034/2063; A61B 2034/2065; A61B 8/14; A61B 8/4245; A61B 6/5247; A61B 34/20; A61B 5/06; A61B 2090/376
See application file for complete search history.

(56) References Cited

U.S. PATENT DOCUMENTS

| | | | |
|---|---|---|---|
| 9,256,947 | B2 | 2/2016 | Gauthier |
| 2002/0107447 | A1 | 8/2002 | Suorsa |
| 2006/0247520 | A1* | 11/2006 | McGee ............... A61B 5/062 600/434 |
| 2009/0185657 | A1* | 7/2009 | Klingenbeck-Regn ..................... A61B 6/4441 378/14 |
| 2009/0207965 | A1 | 8/2009 | Sakaguchi |
| 2012/0245458 | A1* | 9/2012 | Gogin .................. A61B 6/12 600/424 |
| 2012/0296202 | A1 | 11/2012 | Mountney |
| 2013/0259341 | A1 | 10/2013 | Mountney |
| 2014/0121502 | A1 | 5/2014 | Vignon |
| 2015/0087978 | A1* | 3/2015 | Wada ................... A61B 8/44 600/440 |
| 2015/0223773 | A1* | 8/2015 | John ................... A61B 6/503 600/424 |
| 2015/0257730 | A1* | 9/2015 | Masumoto ........... A61B 8/466 600/440 |

FOREIGN PATENT DOCUMENTS

| | | |
|---|---|---|
| WO | 2010073165 A1 | 7/2010 |
| WO | 2011070477 A1 | 6/2011 |
| WO | 2011070492 A1 | 6/2011 |
| WO | 2014087324 A1 | 6/2014 |

OTHER PUBLICATIONS

Sündermann, Simon H. et al "Safety and feasibility of novel technology fusing echocardiography and fluoroscopy images during MitraClip interventions", Eurointervention Clinical Research, 2013.

* cited by examiner

GUIDANCE DEVICE FOR A TEE PROBE

CROSS-REFERENCE TO PRIOR APPLICATIONS

This application is the U.S. National Phase application under 35 U.S.C. § 371 of International Application No. PCT/EP2015/062938, filed on Jun. 10, 2015, which claims the benefit of European Patent Application No. 14172641.4, filed on Jun. 17, 2014. These applications are hereby incorporated by reference herein.

FIELD OF THE INVENTION

The present invention relates to a guidance device for a TEE probe, a medical imaging system, a method for guiding a TEE probe, a computer program element for controlling such device and a computer readable medium having stored such computer program element.

BACKGROUND OF THE INVENTION

For providing a monitoring of medical procedures that require more soft-tissue information than provided by e.g. standard X-ray imaging, transesophageal echocardiography (TEE) information is employed. TEE imaging, which is a form of ultrasound imaging, is able to show an interventional device and its surrounding anatomy simultaneously and provides excellent detail of anatomical structure and function that is often lacking in live X-ray images.

Often, a combination of X-ray fluoroscopy and TEE imaging is used to monitor medical procedures. Thereto, US 2012/245458 A1 discloses to detect and track an interventional device in a 2D fluoroscopy image and to steer a TEE ultrasound probe beam towards this device. The ultrasound probe is registered in the fluoroscopy image and the registering includes the estimation of the position and of the orientation of the probe relative to the fluoroscopy. WO2014/087324 A1 discloses an automatic steering of the ultrasound plane, in order to always present a moving object of interest (e.g. interventional device) inside the ultrasound plane. In this effect, a processing unit is configured to calculate the ultrasound image plane using a first line or vector from the TEE probe to the X-ray source and a second line or vector from the TEE probe to the interventional device.

However, interventional devices, as e.g. catheters, are due to their acoustic properties hardly visible in TEE images or rendered with artifacts.

SUMMARY OF THE INVENTION

Hence, there may be a need to improve the visibility of an interventional device in TEE image data.

The problem of the present invention is solved by the subject-matters of the independent claims, wherein further embodiments are incorporated in the dependent claims. It should be noted that the following described aspects of the invention apply for the guidance device for a TEE probe, for the medical imaging system, for the method for guiding a TEE probe, for the computer program element, and for the computer readable medium.

According to the present invention, a guidance device for a TEE probe is presented. The guidance device for a TEE probe comprises an image data provision unit and a processing unit.

The image data provision unit is configured to provide first image data showing an interventional device and a TEE probe in an initial position and orientation. In an example, the first image data are fluoroscopy X-ray image data. The interventional device may be a catheter.

The processing unit is configured to determine a centerline of the interventional device in the first image data. In an example, the centerline of the interventional device is determined in 3D, based on a single X-ray image, a bi-plane X-ray image and/or an alternative 3D tracking technology as e.g. electromagnetic tracking or optical shape sensing. Optical shape sensing measures the 3D shape of a several twisted fibers that are packed into a single wire by analyzing the reflected laser light that is coupled into the fibers.

The processing unit is further configured to determine a plane orthogonal to a tangent of the centerline as viewing plane, as the visibility of the interventional device strongly depends on the orientation of the TEE probe with respect to the interventional device. An even surface of the interventional device only reflects an echo signal and provides hardly any back-scattering signal. Therefore, the interventional device is only fully visible in the TEE image, if the TEE signal propagation vector is approximately collinear with the surface normal to the interventional device. As a result, a plane orthogonal to the tangent of at least a centerline segment defines the optimal locations for the TEE probe. Optimal means that the TEE signal propagation vector is approximately collinear with a surface normal to the interventional device. In other words, the viewing plane may be defined as plane of optimal locations for the TEE probe in view of the visibility of the interventional device. In an example, the processing unit is configured to determine the viewing plane based on 2D segmentation of the interventional device.

The processing unit is configured to calculate an imaging plane and an imaging orientation of the TEE probe to lie approximately in the viewing plane. The imaging plane and imaging orientation of the TEE probe may be defined as current location and orientation of the TEE probe. The imaging plane and imaging orientation of the TEE probe are to be arranged to lie approximately in the viewing plane as plane of optimal locations for the TEE probe in view of the visibility of the interventional device. Optimal means that the TEE signal propagation vector is approximately collinear with a surface normal to the interventional device. As a result, an optimal plane and orientation of the TEE probe is found, whereby the imaging orientation means an imaging angle or opening angle of an e.g. cone- or fan-shaped imaging field of view of the TEE probe.

In an example, the processing unit is configured to calculate a position of the TEE probe, such that the interventional device lies within the cone- or fan-shaped imaging field of the TEE probe. In an example, the processing unit is configured to calculate a position of the TEE probe such that the interventional device lies in the center of gravity of the cone- or fan-shaped imaging field of the TEE probe. Thereby, the visibility of the interventional device in TEE image data is further improved.

The processing unit is further configured to provide the calculated data as guidance data. In an example, the processing unit is configured to communicate the calculated data to a user as indication how to change the position and/or orientation of the TEE probe for an optimized TEE view. In an example, an optimal view map is calculated and displayed based on the extracted centerline, showing positions and orientations of the TEE probe for which the TEE ultrasonic propagation direction is approximately orthogonal to the catheter surface and therefore, an optimum visibility of the catheter is to be expected.

In other words and exemplarily, the guidance device automatically presents an optimal TEE probe pose to an operator based on an image-based optimization of the orientation and position of the TEE probe relative to the interventional device. Thereby, the guidance device helps to guide the TEE probe to another orientation and/or position to provide TEE image data with an improved visibility of the interventional device for improved navigation in complex interventions. Further, all relevant information can be shown in one single view where information is co-registered.

The best view, position and/or orientation of the TEE probe may be registered and superimposed to the first image data as indication for an operator how to adapt or where to move the TEE probe, or may be communicated to the interventional staff by other means. In an example, the processing unit is configured to combine the imaging position and/or orientation of the TEE probe with the first image data, and the guidance device further comprises a display unit to display the combination.

The guidance device may further comprise a control unit configured to provide signals for a moving mechanism to move the TEE probe from the initial position and orientation to the imaging position and/or orientation. In an example, the change of the orientation of the TEE probe comprises only an electronically adapting of the orientation of the TEE probe, which means an electronically adjusting of its measurement plane without moving the probe. A combination of moving and electronically adapting may give even better results.

In an example, the processing unit is configured to exclude unsuitable positions of the TEE probe as imaging positions. Therefore, a calculation of the optimal view, position and/or orientation may be constrained by a segmentation or model of e.g. the esophagus, which excludes non-accessible positions of the TEE probe.

According to the present invention, also a medical imaging system is presented. The medical imaging system comprises an image data acquisition device, a TEE probe, a guidance device for the TEE probe, and a display unit. The image data acquisition device is configured to acquire first image data to be provided by the image data provision unit of the guidance device. The TEE probe is configured to provide second image data and the display unit is configured to provide guidance data.

According to the present invention, also a method for guiding a TEE probe is presented. It comprises the following steps, not necessarily in this order:

a) providing first image data showing an interventional device and a TEE probe in an initial position and orientation, b) determining a centerline of the interventional device in the first image data, c) determining a plane orthogonal to a tangent of the centerline as viewing plane, d) calculating at least an imaging plane and an imaging orientation of the TEE probe to lie approximately in the viewing plane, and e) providing the calculated data as guidance data.

In an example, not only the imaging plane and an imaging orientation, but also a position of the TEE probe is calculated such that the interventional device lies within an e.g. cone- or fan-shaped imaging field of the TEE probe, or preferably lies in the center or center of gravity of the imaging field.

In an example, the calculated data are communicated to a user as indication how to change the position and/or orientation of the TEE probe for an optimized TEE view. In an example, the imaging position and/or orientation of the TEE probe is combined with the first image data and also communicated to a user.

In an example, a moving mechanism moves the TEE probe from the initial position and orientation to the imaging position and/or orientation and/or changes the orientation of the TEE probe by an electronically adapting of the orientation without a moving of the TEE probe.

According to the present invention, also a computer program element is presented, wherein the computer program element comprises program code means for causing a guidance device as defined in the independent device claim to carry out the steps of the method for guiding a TEE probe as defined in the independent method claim, when the computer program is run on a computer controlling the guidance device.

It shall be understood that the guidance device for a TEE probe, the medical imaging system, the method for guiding a TEE probe, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
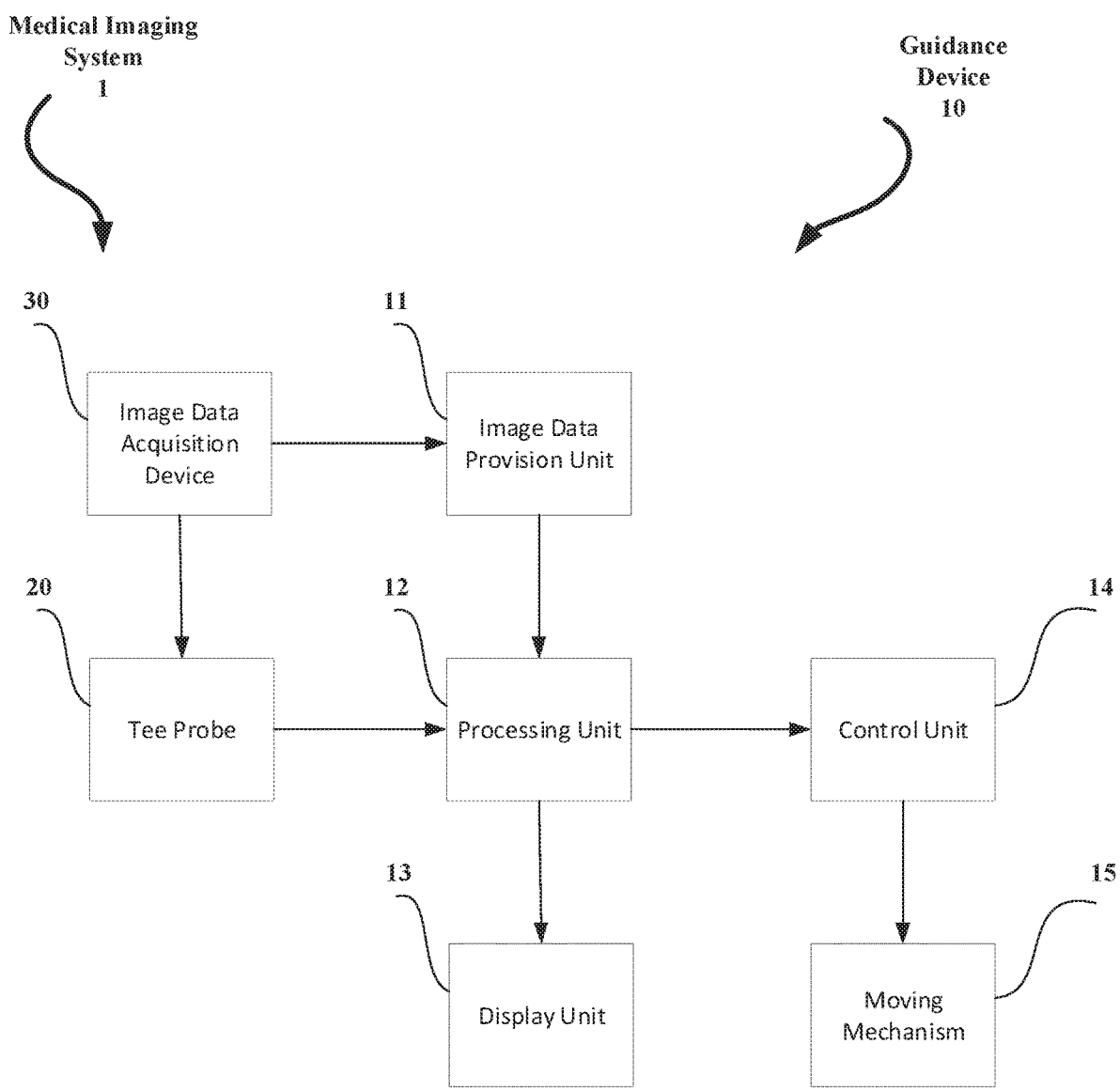
FIG. 1 shows a schematic drawing of an example of a medical imaging system according to the invention.

FIG. 1 shows schematically and exemplarily an embodiment of a medical imaging system 1 according to the invention. The medical imaging system 1 comprises an image data acquisition device 30, a TEE transducer or probe 20, a guidance device 10 for the TEE probe 20, and a display unit 13.

The image data acquisition device 30 acquires first image data, the TEE probe 20 provides second image data and the display unit 13 provides guidance data to be explained in the following. The first image data are X-ray fluoroscopy image data.

The guidance device 10 for a TEE probe 20 comprises an image data provision unit 11 and a processing unit 12. The image data provision unit 11 provides the first image data of the image data acquisition device 30. The first image data show an interventional device 40 and the TEE probe 20 in an initial position and orientation. The interventional device 40 is a catheter. The image data provision unit 11 is connected with the image data acquisition device 30 and the processing unit 12.

The processing unit 12 is further connected with the image data provision unit 11, the TEE probe 20, the display unit 13 and a control unit 14. The processing unit 12 determines a centerline of the interventional device 40 in the first image data. The centerline may be determined in 3D based on a single X-ray image, a bi-plane X-ray image and/or the like.

Figure 2A:
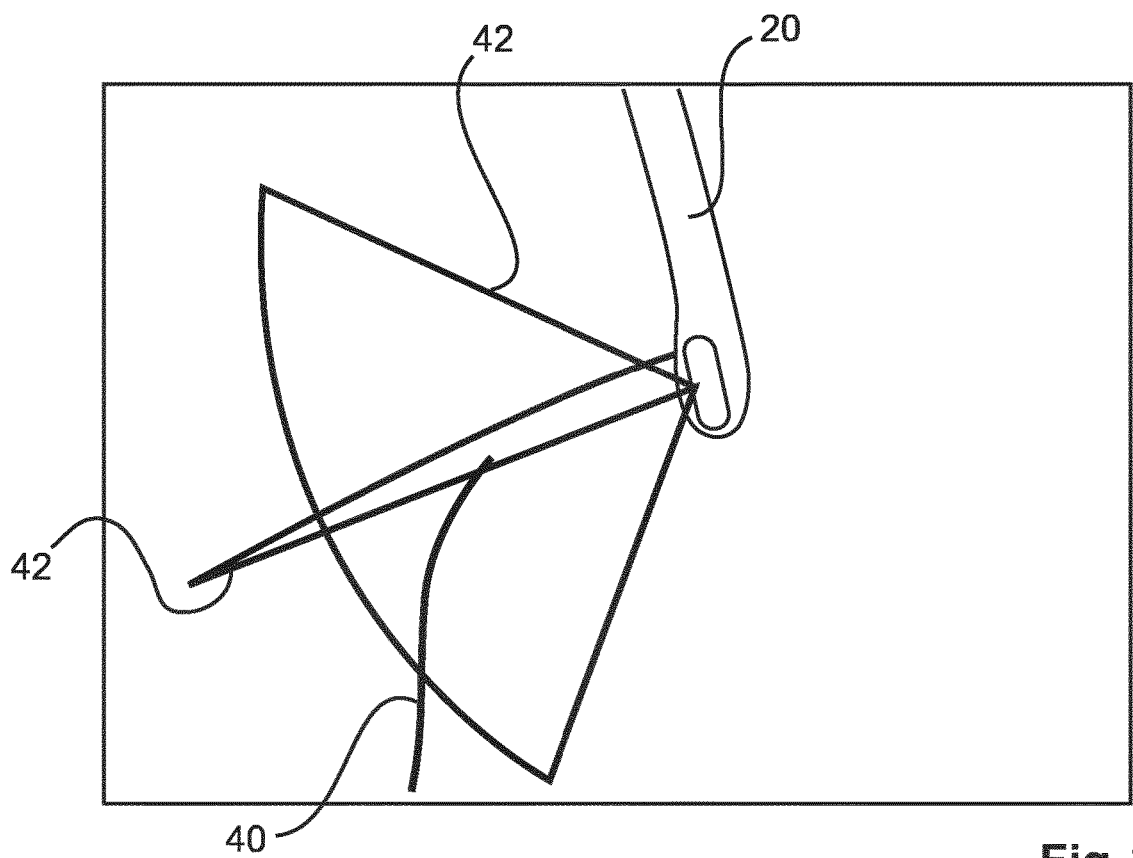
FIG. 2 shows a schematic drawing of two X-ray images showing an interventional device and a TEE probe.
Figure 2B:
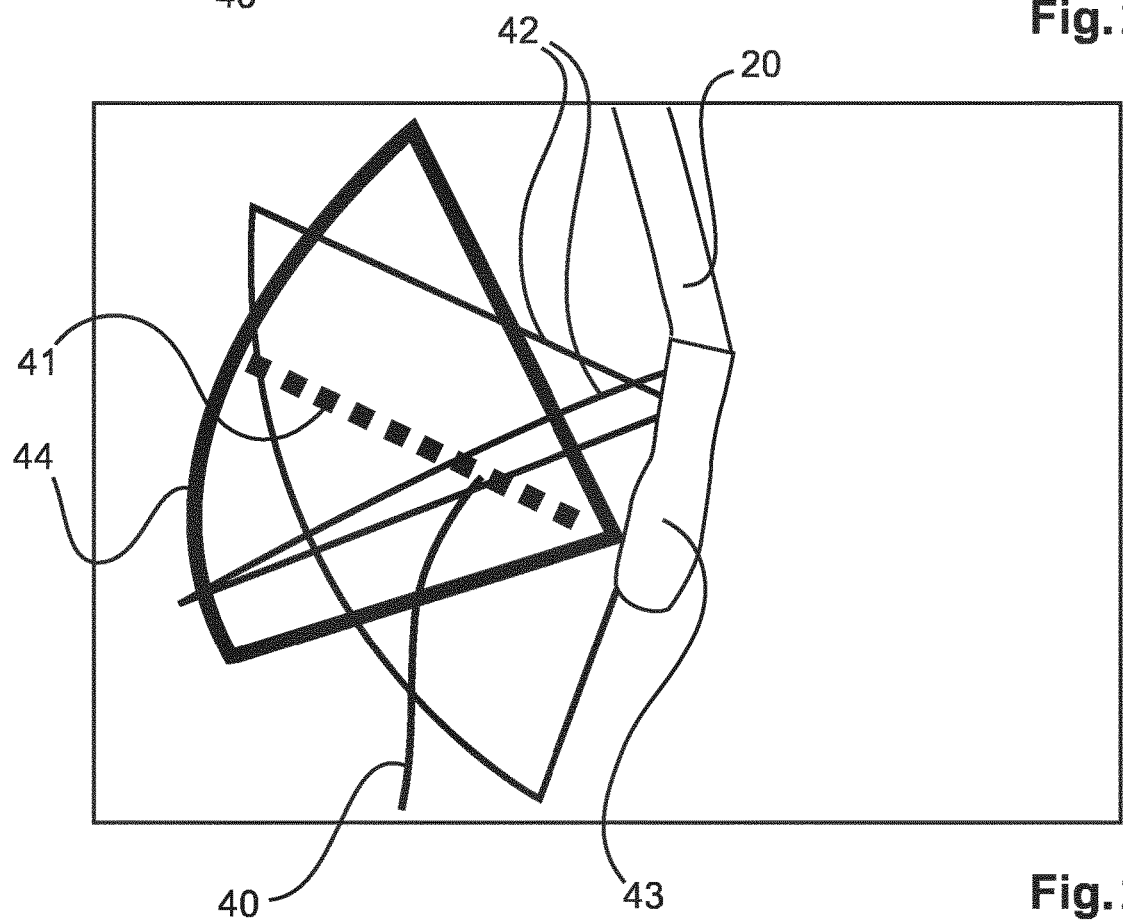

The TEE probe 20, the interventional device 40 and a plane 41 orthogonal to a tangent of the centerline of the interventional device 40 are shown in FIGS. 2a and 2b. The processing unit 12 determines the plane 41 orthogonal to a tangent of the centerline as viewing plane. The processing unit 12 determines the viewing plane based on 2D segmentation of the interventional device 40. The plane 41 orthogonal to the tangent of the centerline defines the optimal locations for the TEE probe 20, as the TEE signal propagation vector is then approximately collinear with a surface normal to the interventional device 40.

The processing unit 12 calculates an imaging plane and an imaging orientation of the TEE probe 20 to lie approximately in the viewing plane. Thereby, the optimal plane and orientation of the TEE probe 20 is found, whereby the imaging orientation means an imaging angle or opening angle of an e.g. cone-shaped imaging field of view of the TEE probe 20. Optimal means that the TEE signal propagation vector is then approximately collinear with a surface normal to the interventional device. The processing unit may further calculate a position of the TEE probe 20, such that the interventional device 40 lies within the cone-shaped imaging field of the TEE probe 20. The processing unit may further calculate a position of the TEE probe 20 such that the interventional device 40 lies in the center of gravity of the cone-shaped imaging field of the TEE probe 20.

The processing unit 12 provides the calculated data as guidance data and communicates them to a user as indication how to change the position and/or orientation of the TEE probe 20 for an optimized TEE view. Also an optimal view map is calculated and displayed on the display unit 13. The best view, position and/or orientation of the TEE probe 20 is superimposed onto the first image data as indication for an operator how to adapt or where to move the TEE probe 20.

The TEE probe 20 can then be moved to the optimal TEE probe 20 pose. Therefore, the guidance device 10 further comprises the control unit 14 to provide signals for a moving mechanism 15 to move the TEE probe 20 from the initial position and orientation to the imaging position and/or orientation. The control unit 14 is therefore connected to the moving mechanism 15.

The change of the orientation of the TEE probe 20 can also comprises an only electronically adapting of the orientation of the TEE probe 20, which means an electronically adjusting of its measurement plane without moving the TEE probe 20.

Thereby, the guidance device 10 automatically presents an optimal TEE probe 20 pose to an operator based on an image-based optimization of the orientation and position of the TEE probe 20 relative to the interventional device 40. As a result, the guidance device 10 helps to guide the TEE probe 20 to another orientation and/or position to provide TEE image data with an improved visibility of the interventional device 40 for improved navigation in complex medical interventions.

FIG. 2a shows a drawing of an X-ray image showing a catheter as interventional device 40 and the TEE probe 20 in its initial position and orientation and with its initial two cone-shaped fields of view 42 orthogonal to each other.

FIG. 2b shows a further drawing of the same X-ray image, but the optimal imaging position of the TEE probe 20 is now registered and superimposed on the X-ray image as overlay 43 to help the operator to move the TEE probe 20 to the optimal imaging position to achieve optimal image data of the interventional device 40. FIG. 2b further shows an optimal cone-shaped field of view 44 of the TEE probe 20 also superimposed on the X-ray image. FIG. 2b further shows a line corresponding to a plane 41 orthogonal to a tangent of the centerline of the catheter, whereby this plane is also the optimal viewing plane of the TEE probe 20, as the TEE signal propagation vector is then approximately collinear with a surface normal to the catheter. A subset set of the optimal viewing plane can be obtained by a 2D catheter segmentation and centerline extraction, which provides an intersecting line of the optimal viewing plane with a detector plane.

Figure 3:
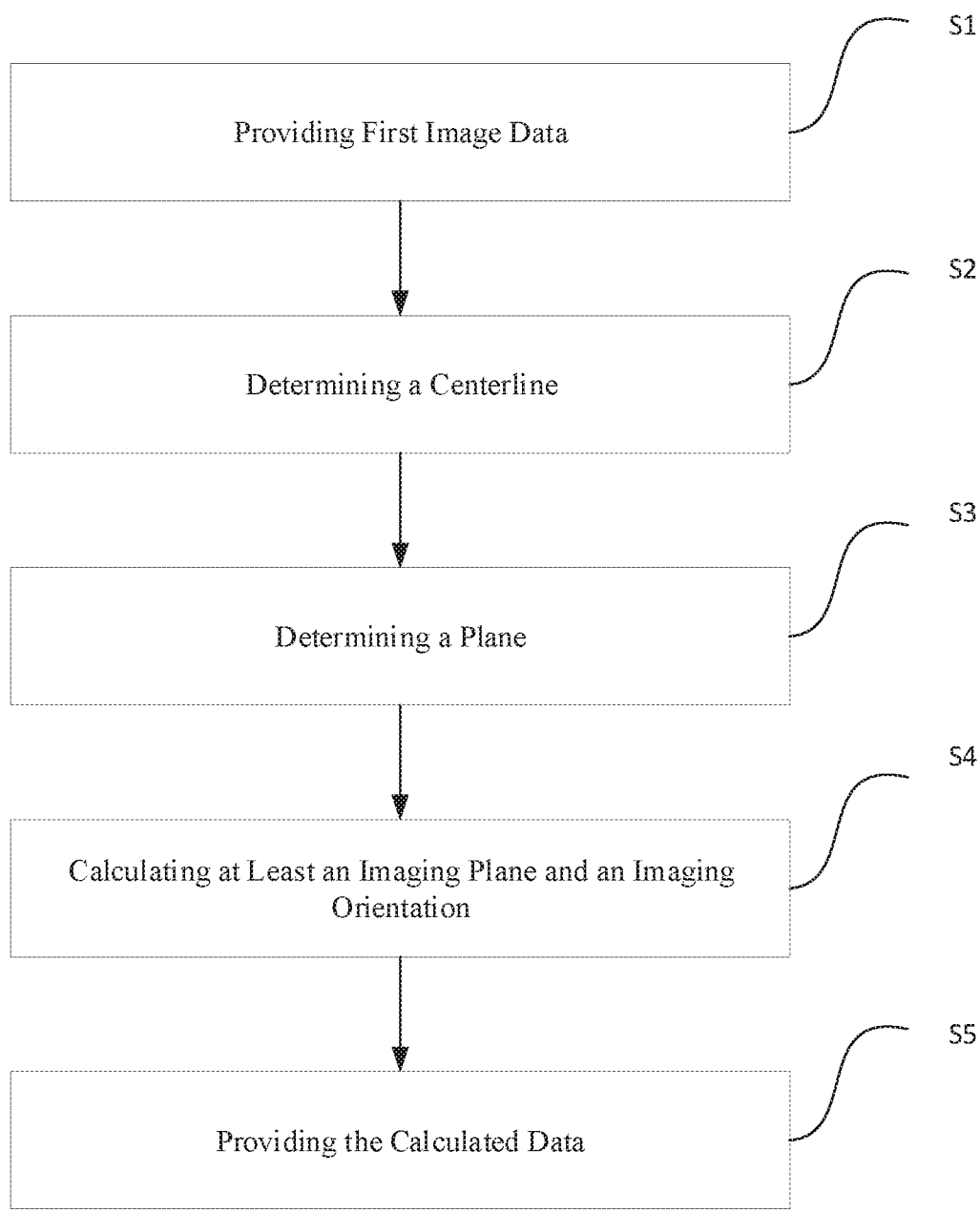
FIG. 3 shows basic steps of an example of a method for guiding a TEE probe.

FIG. 3 shows basic steps of an example of a method for guiding the TEE probe 20. It comprises the following steps, not necessarily in this order:

in a first step S1, providing first image data showing an interventional device 40 and a TEE probe 20 in an initial position and orientation, in a second step S2, determining a centerline of the interventional device 40 in the first image data, in a third step S3, determining a plane 41 orthogonal to a tangent of the centerline as viewing plane, in a fourth step S4, determining calculating at least an imaging plane and an imaging orientation of the TEE probe 20 to lie approximately in the viewing plane, and in a fifth step S5, determining providing the calculated data as guidance data.

Not only the imaging plane and the imaging orientation, but also the position of the TEE probe 20 can be calculated such that the interventional device 40 lies within the cone-shaped imaging field of the TEE probe, or preferably lies in the center or center of gravity of the imaging field. The calculated data are communicated to a user as indication how to change the position and/or orientation of the TEE probe 20 for an optimized TEE view. The imaging position and/or orientation of the TEE probe 20 is combined with the first image data and also communicated to a user. The moving mechanism 15 moves the TEE probe 20 from the initial position and orientation to the imaging position and/or orientation and/or changes the orientation of the TEE probe 20 by an electronically adapting of the orientation without moving of the TEE probe 20.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A guidance device for a transesophageal echocardiography (TEE) probe, comprising:
    a memory that stores an executable computer program; and
    a processor that executes the computer program, wherein, when executed by the processor, the computer program causes the guidance device for the TEE probe to implement a process that includes:
    receiving first image data from an image data acquisition device showing an interventional device and the TEE probe in an initial position and orientation;
    determining a centerline of the interventional device in the first image data;
    determining a plane orthogonal to a tangent of the centerline as an optimal viewing plane for the TEE probe in the first image data;
    calculating as calculated data an imaging plane and an imaging orientation of the TEE probe for acquiring second image data showing the interventional device, wherein the imaging plane and the imaging orientation are projected to lie approximately in the optimal viewing plane; and
    providing the calculated data as guidance data to guide the TEE probe to the imaging plane and the imaging orientation of the TEE probe lying approximately in the optimal viewing plane, at which a TEE signal propagation vector from the TEE probe is approximately collinear with a surface orthogonal to the tangent of the centerline of the interventional device.

2. The guidance device according to claim 1, wherein the second image data provided by the TEE probe lie in a cone- or fan-shaped imaging field, wherein the process implemented when the processor executes the computer program further includes calculating a position of the TEE probe, such that the interventional device lies within the cone- or fan-shaped imaging field of the TEE probe.

3. The guidance device according to claim 2, wherein the process implemented when the processor executes the computer program further includes calculating the position of the TEE probe such that the interventional device lies in a center of gravity of the cone- or fan-shaped imaging field of the TEE probe.

4. The guidance device according to claim 1, wherein the process implemented when the processor executes the computer program further includes communicating the calculated data to a user as an indication of how to change position and/or orientation of the TEE probe to the imaging plane and the imaging orientation.

5. The guidance device according to claim 4, wherein the change of the orientation of the TEE probe comprises electronically adapting the orientation of the TEE probe and/or moving the TEE probe.

6. The guidance device according to claim 1, wherein the process implemented when the processor executes the computer program further includes combining an imaging position and/or orientation of the TEE probe with the first image data.

7. The guidance device according to claim 1, wherein the first image data are fluoroscopy image data.

8. The guidance device according to claim 1, wherein the centerline of the interventional device is determined in 3D based on a single X-ray image, a bi-plane X-ray image and/or optical shape sensing.

9. The guidance device according to claim 1, wherein the process implemented when the processor executes the computer program further includes determining the optimal viewing plane based on 2D segmentation of the interventional device.

10. The guidance device according to claim 1, wherein the process implemented when the processor executes the computer program further includes excluding unsuitable positions of the TEE probe as imaging positions.

11. The guidance device according to claim 1, further comprising a control unit configured to provide signals for a moving mechanism to move the TEE probe from the initial position and orientation to the imaging plane and the imaging orientation.

12. A medical imaging system, comprising:
the image data acquisition device;
the TEE probe;
the guidance device for the TEE probe according to claim 1; and
a display unit,
wherein the image data acquisition device is configured to acquire the first image data to be provided by the guidance device,
wherein the TEE probe is configured to provide the second image data, and
wherein the display unit is configured to provide guidance data of the guidance device.

13. A non-transitory computer readable medium that stores a computer program for controlling a guidance device for a transesophageal echocardiography (TEE) probe, wherein, when executed by a processor, the computer program causes the guidance device for the TEE probe to implement a process that includes:
receiving first image data from an image data acquisition device showing an interventional device and the TEE probe in an initial position and orientation;
determining a centerline of the interventional device in the first image data;
determining a plane orthogonal to a tangent of the centerline as an optimal viewing plane for the TEE probe in the first image data;
calculating as calculated data an imaging plane and an imaging orientation of the TEE probe for acquiring second image data showing the interventional device, wherein the imaging plane and the imaging orientation are projected to lie approximately in the optimal viewing plane; and
providing the calculated data as guidance data to guide the TEE probe to the imaging plane and the imaging orientation of the TEE probe lying approximately in the optimal viewing plane, at which a TEE signal propagation vector from the TEE probe is approximately collinear with a surface orthogonal to the tangent of the centerline of the interventional device.

14. The non-transitory computer readable medium of claim 13, wherein second image data provided by the TEE probe lie in a cone- or fan-shaped imaging field, wherein the process implemented when the processor executes the computer program further includes calculating a position of the TEE probe, such that the interventional device lies within the cone- or fan-shaped imaging field of the TEE probe.

15. The non-transitory computer readable medium of claim 14, wherein the process implemented when the processor executes the computer program further includes calculating the position of the TEE probe such that the interventional device lies in a center of gravity of the cone- or fan-shaped imaging field of the TEE probe.

16. The non-transitory computer readable medium of claim 13, wherein the process implemented when the processor executes the computer program further includes communicating the calculated data to a user as an indication of how to change position and/or orientation of the TEE probe to the imaging plane and the imaging orientation.

17. The non-transitory computer readable medium of claim 16, wherein the change of the orientation of the TEE probe comprises electronically adapting the orientation of the TEE probe and/or moving the TEE probe.

18. The non-transitory computer readable medium of claim 13, wherein the process implemented when the processor executes the computer program further includes combining an imaging position and/or orientation of the TEE probe with the first image data.

19. The non-transitory computer readable medium of claim 13, wherein the first image data are fluoroscopy image data.

20. The non-transitory computer readable medium of claim 13, wherein the process implemented when the processor executes the computer program further includes determining the optimal viewing plane based on 2D segmentation of the interventional device.

* * * * *